United States Patent
Woodfin

(10) Patent No.: US 7,244,872 B2
(45) Date of Patent: Jul. 17, 2007

(54) PRODUCTION OF OLEFINS

(75) Inventor: William Terence Woodfin, North Waltham (GB)

(73) Assignee: Ineos Europe Limited, Hampshire (GB)

(*) Notice: Subject to any disclaimer, the term of this patent is extended or adjusted under 35 U.S.C. 154(b) by 150 days.

(21) Appl. No.: 10/502,545

(22) PCT Filed: Feb. 13, 2003

(86) PCT No.: PCT/GB03/00637

§ 371 (c)(1), (2), (4) Date: Jul. 27, 2004

(87) PCT Pub. No.: WO03/070672

PCT Pub. Date: Aug. 28, 2003

(65) Prior Publication Data

US 2005/0089299 A1   Apr. 28, 2005

(30) Foreign Application Priority Data

Feb. 22, 2002 (GB) ................................. 0204140.8

(51) Int. Cl.
*C07C 4/02* (2006.01)
*C07C 5/373* (2006.01)
*C07C 5/333* (2006.01)

(52) U.S. Cl. ................ 585/651; 585/652; 585/653; 585/658; 585/660

(58) Field of Classification Search ........ 585/651–653, 585/658, 660
See application file for complete search history.

(56) References Cited

U.S. PATENT DOCUMENTS

| 3,329,605 | A | | 7/1967 | Tokuhisa et al. |
| 4,143,521 | A | | 3/1979 | Pano et al. |
| 4,617,109 | A | | 10/1986 | Wells et al. |
| 4,912,282 | A | | 3/1990 | Klaus |
| 5,382,741 | A | * | 1/1995 | Astbury et al. ............. 585/652 |
| 6,395,944 | B1 | * | 5/2002 | Griffiths et al. ............. 585/324 |

FOREIGN PATENT DOCUMENTS

| DE | 3433088 A1 | 3/1985 |
| DE | 42 41 464 A1 | 3/1994 |

(Continued)

OTHER PUBLICATIONS

"Industry Briefs/Petrochemicals . . . BASF and Sontrach"; *Oil & Gas Journal*; vol. 97, No. 46; pp. 34-35 (1999) (Abstract).

(Continued)

*Primary Examiner*—Glenn Caldarola
*Assistant Examiner*—In Suk Bullock
(74) *Attorney, Agent, or Firm*—Nixon & Vanderhye

(57) ABSTRACT

Process for producing mono-olefins from a paraffin-containing hydrocarbon feed, comprising partially combusting a mixture of the hydrocarbon feed and a molecular oxygen-containing gas in contact with a catalyst capable of supporting combustion beyond the normal fuel rich limit of flammability and subsequently separating the products of the combustion. Energy for the separation is provided by a cogeneration process which simultaneously produces thermal energy and mechanical energy by combustion of fuel. The mechanical energy is converted to electricity, and the thermal energy is used to create steam for use in a steam turbine.

11 Claims, 2 Drawing Sheets

FOREIGN PATENT DOCUMENTS

| | | |
|---|---|---|
| EP | 0 332 289 B1 | 3/1995 |
| EP | 0 529 793 B1 | 5/1996 |
| EP | 0 709 446 A2 | 5/1996 |
| GB | 1 351 623 | 5/1974 |
| GB | 2 027 739 A | 2/1980 |
| JP | 50-24918 | 6/1973 |
| JP | 51-13122 | 7/1974 |
| JP | 57-165325 | 10/1982 |
| JP | 62-146990 | 6/1987 |
| RU | 1824420 A1 | 6/1993 |
| SU | 160168 | 1/1964 |
| WO | WO 94/04632 | 3/1994 |
| WO | WO 00/14035 | 3/2000 |
| WO | WO 00/15587 A | 3/2000 |
| WO | WO 01/04236 A | 1/2001 |

OTHER PUBLICATIONS

"Compressor Serves Single-Train Ethylene Plant"; *Oil & Gas Journal*; vol. 70; p. 64 (1972) (Abstract).

"Stone & Webster for Reliance Cracker"; *Chemical Week*; pp. 40 (1992) (Abstract).

"Gas Turbine Integration Reduces Ethylene Plant's Energy Needs"; *Oil & Gas Journal*; pp. 55-60 (1992) (Abstract).

"Quantum Cracker Set for Year-End"; *Chemical Marketing Reporter*; pp. 5 (1990) (Abstract).

Albano J.V., et al; "Gas Turbine Integration in Ethylene Plants"; *AIChE 4th Ethylene Producers Conference* (New Orleans Mar. 31-Apr. 1, 1992) *Proceedings*; V1; pp. 236-263 (1992) (Abstract).

Cen, K., et al; "Research on Biomass Gasification Gas/Steam Cogeneration System Using a Circulating Fluidized Bed"; *Proc. Int. Conf. Fluid. Bed Combustion*; vol. 1; pp. 207-210 (1993) (Abstract).

Chan, P.S.; "Impact of Energy-savings Features on Ethylene Plant Energy Consumption"; *1989 AIChE Spring Natl. Meet.* (Houston Apr. 2-6, 1989) *Prepr.*; N.34p 23P (1989) (Abstract).

Cooke, D.H., et al; "Cogenerative, Direct Exhaust Integration of Gas Turbines in Ethylene Production"; *J. Eng. Gas Turbines Power*; vol. 113, No. 2; pp. 212-220 (1991) (Abstract).

Cooke, D.H., et al; "Cognerative, Direct Exhaust Integration of Gas Turbines in Ethylene Production"; *American Society of Mechanical Engineers (Paper) Publ. by American Society of Mechanical Engineers (ASME)*; New York, NY, USA; GT-139; 10 p (1990) (Abstract).

Crawshaw, D.E.; "Unique Charge Gas Compressor Train for the Mossmorran Ethylene Plant"; *CME Chart Mech. Eng.*; vol. 33, No. 9; pp. 65-68 (1986) (Abstract).

Fainberg, V., et al; "Integrated Oil Shale Processing into Energy and Chemicals using Combined-cycle Technology"; *Energy Sources*; vol. 20, No. 6, pp. 465-481 (1998) (Abstract).

Fang, M., et al; "A Multi-product Cogeneration System using Combined Coal Gasification and Combustion"; *Energy*; vol. 23, No. 3; pp. 203-212 (1998) (Abstract).

Frangopoulos, C.A., et al; "Thermoeconomic Operation Optimization of the Hellenic Aspropyrgos Refinery Combined-Cycle Cogeneration System"; *Applied Thermal Engineering*; vol. 16, No. 12, pp. 949-958; (1996) (Abstract).

Fukushima, T., et al; "Gas Turbine Integration in Ethylene Plants"; *ABB Review*; No. 4; pp. 3-14 (1992) (Abstract).

Gaston, J.R., et al; "Integrated Turbine-Compressor Controls Retrofit for an Olefins Unit"; *American Society of Mechanical Engineers (Paper) ASME*, New York, NY USA; 8pp; 95-GT-349 (1995) (Abstract).

Geihsler, V.G.; "Major Effects from Minor Features in Ethylene Plants"; *AIChE Loss Prevention*; 12; pp. 9-12 (1979) (Abstract).

Gillett, F.L.; "Ethylene from NGL Feedstocks"; *Hydrocarbon Process., Int. Ed.*; vol. 63, (2, Sec. 1); pp. 69-72 (1984) (Abstract).

Hull, C.P., et al; "An Experimental Investigation of Catalytic Reaction Under Pressure Swing Operation"; *IChemE Res. Event, Two-Day Symp.*; vol. 2, pp. 562-4; Publisher: Inst. Chem. Eng., Rugby, UK (1994) (Abstract).

Kenney, W.F.; "Combustion-Air Preheat Saves Energy in Olefins Production at Ethylene Plants"; *5th Ind. Energy Conserv. Technol. Annu. Conf.* (Houston Apr. 17-20, 1983): (*Adapt.*) *Oil Gas Journal*; vol. 81, No. 42; pp. 130-132 (1983) (Abstract).

Korosi, A., et al; "Combustion of Oil Shale, Fluidized Coal and Pyrolysis Fuel Oil Residues in a Stationary Gas Turbine"; *VGB Kraftwerkstech*; vol. 64, No. 4; pp. 323-335 (1984) (Abstract).

Liang, F.; Energy Saving Technology in Ethylene Production; *Xiandai Huagong*; vol. 5, No. 5; pp. 12-16 (1984) (Abstract).

Liang, F.; "Energy Saving Technology in Ethylene Production"; *Xiandai Huagong*; vol. 5, No. 5, pp. 12-16 (1985) (Abstract).

Mohr, V.H., et al; "New Developments in Olefins Technology"; *1989 AIChE Spring Natl. Meet.* (Houston Apr. 2-6, 1989); *Prepr.* No. 82a; 35P. (1989) (Abstract).

Morton, J.T., et al; "Fast-Track Controls Retrofit for a Gas & Steam Turbine Propylene Compressor Drive"; *American Society of Mechanical Engineers (Paper) Publ. by ASME*, New York, NY USA, Alberta; p. 1-7; 93-GT-351 (1993) (Abstract).

Orriss, R., et al; "Idemitsu (Petrochenmical Co"s) Chiba Ethylene Plant Proves Modern Technology"; *Oil Gas Journal*; vol. 85, No. 10; pp. 27-30 (1987) (Abstract).

Orriss, R.; "Make that Either/or"; Letters (to the Editor); *Oil Gas Journal*; vol. 85, No. 13; p. 10 (1987).

Siklos, P.; "Ethylene Production"; *Magy. Kem. Lapja*; vol. 52, No. 3; pp. 154-161 (1997) (Abstract).

Solantausta, Y.; "New Arlternatives for Electricity Production"; *Tutkimuksia—Valt. Tek. Tutkimuskeskus*; 703; 137pp (1990) (Abstract).

Tsai, F.W., et al; "Why Retrofit Furnaces?"; *Hydrocarbon Processing*; vol. 64, No. 8; pp. 41-47 (1985) (Abstract).

Verde, L, et al; "Balance Energy in Ethylene Plants"; *Chem. Eng. Monogr.*; vol. 10; pp. 1-21 (1979) (Abstract).

Ward, M.; "Emphasis on Retrofits as Cracker Building Wanes"; *Eur. Chem. News*; 47(Process Rev. Suppl.); pp. 6-8 (1986) (Abstract).

Weismantel, G.E.; "Heavy Oil Cracking"; *Petroleum Processing Handbook*; pp. 480-515 of 789 p. (1992) (Abstract).

Wells, T.A.; "Utilities Export is a Valuable Olefins Unit Byproduct"; *Oil Gas Journal*; vol. 80, No. 24; pp. 63-68 (1982) (Abstract).

Wing, M.; "Why not Crack Crude?"; *Chemtech*; vol. 10, No. 1; pp. 20-22 (1980) (Abstract).

* cited by examiner

PRODUCTION OF OLEFINS

This application is the U.S. National Phase of International Application PCT/GB03/00637, filed 13 Feb. 2003, which designated the U.S.

The present invention relates to a process for the production of olefins from hydrocarbons, more particularly to an energy-efficient process in which the hydrocarbons are treated to autothermal cracking.

BACKGROUND OF THE INVENTION

Olefins (ethylene, propylene and butenes) production is a very energy-intensive process. Current steam cracking technology involves a process furnace to provide energy to crack feeds to olefin products, heat recovery from the products, a large compressor to pressurise the product stream to relatively high pressures (3-500 psig), and distillation to separate and purify the products. The process furnace is a relatively inefficient way to provide the heat of cracking: only about 40% to 50% of the heat released in the process furnace is used in the cracking reactions. The remainder of the furnace heat is recovered in the furnace convective section and integrated with the process gas heat recovery systems to provide high pressure steam to drive the reactor effluent and refrigeration compressors. Any additional energy (in the form of high pressure steam) is typically provided by auxiliary boilers. Steam cracking suffers from the disadvantage that providing compressor energy through such a steam cycle is thermodynamically inefficient, converting only about 25% of the thermal energy of the fuel into useful shaftwork. This, combined with the low efficiency of the process furnace, makes the production of olefins very fuel-intensive.

One way of improving the efficiency of such processes is to provide the heat for cracking by cogeneration (using both gas and steam turbines to provide energy), which is up to 55% efficient in converting fuel thermal energy into usable shaftwork. An example of this is disclosed in WO 01/04236, in which the steam cracking process is characterised in that the energy source to heat the hydrocarbon mixture is provided by a cogeneration unit. The cogeneration unit simultaneously produces thermal energy and mechanical energy by combustion of fuel provided from the cracked hydrocarbons; the mixture of hydrocarbons and steam are subjected to preheating by the thermal energy, whilst the mechanical energy is converted to electricity by an alternator or energy generator, which is then the used to heat the hydrocarbon mixture to the required cracking temperature.

U.S. Pat. No. 4,912,282 discloses a process for cracking hydrocarbons in which a mixture of fuel and an oxygen-containing gas is combusted in a cracking furnace to produce heat for cracking the hydrocarbons. The oxygen-containing gas comprises a mixture of preheated air and the expanded waste gas from a gas turbine, which has been fed with the product of combusting compressed air and fuel in a gas generator. The gas turbine drives electric generators, which power the compressors used in the process.

Whilst the use of gas turbines as described above improves the efficiency of such cracking processes, conventional steam-cracking processes are essentially self-sufficient in energy, with a significant proportion (for example 60% or more) of the total heat required for the whole process being available from the exhaust gases of the furnace and cooling of the cracked products. Accordingly the additional heat required, which is the part to which a cogeneration process can be applied, is relatively small (for example 40% or less), meaning that the overall energy efficiency gains available are also relatively limited, perhaps of the order of 15%.

Autothermal cracking is a new route to olefins in which the hydrocarbon feed is mixed with oxygen and passed over a catalyst. Combustion is initiated on the catalyst surface and the heat required to raise the reactants to process temperature and to carry out the endothermic cracking process is generated in situ. As a result, there is no need for a process furnace. Such a process is described for example in EP 332289B; EP-529793B; EP-A-0709446 and WO 00/14035.

SUMMARY OF THE INVENTION

We have found that incorporating a cogeneration step into an autothermal cracking process can result in substantially greater energy efficiency gains than are generally possible when it is incorporated into a conventional steam cracking process.

Accordingly the present invention provides a process for the production of mono-olefins from a paraffin-containing hydrocarbon feed, comprising a partially combusting a mixture of the hydrocarbon feed and a molecular oxygen-containing gas in contact with a catalyst capable of supporting combustion beyond the normal fuel rich limit of flammability and subsequently separating the products of said combustion, wherein energy for the separation is provided by a cogeneration process which simultaneously produces thermal energy and mechanical energy by combustion of fuel, the mechanical energy being converted to electricity, and the thermal energy being used to create steam for use in a steam turbine.

Usually prior to separating the products of said combustion the products are compressed which facilitates the separation and purification of the products. In a preferred embodiment of the invention the energy for the compression is also provided by the cogeneration process.

Accordingly the present invention also provides a process for the production of mono-olefins from a paraffin-containing hydrocarbon feed, comprising a first step of partially combusting a mixture of the hydrocarbon feed and a molecular oxygen-containing gas in contact with a catalyst capable of supporting combustion beyond the normal fuel rich limit of flammability and subsequent steps of compressing and separating the products of said combustion, wherein energy for the separation and compression steps is provided by a cogeneration process which simultaneously produces thermal energy and mechanical energy by combustion of fuel, the mechanical energy being converted to electricity, and the thermal energy being used to create steam for use in a steam turbine.

We have found that the invention can reduce the fuel requirement of an autothermal cracking process by as much as 40%, substantially more than the gain when cogeneration is applied to a conventional steam-cracking process. As autothermal cracking is itself more efficient than conventional steam-cracking, the fuel requirement of the process of the invention may be as little as one third of that of a conventional steam cracking process; even a conventional steam-cracking process incorporating cogeneration theoretically requires almost three times as much fuel.

Preferably the fuel for the cogeneration comprises one of the products of the separation process. It is also preferred that the mechanical and thermal energy are provided by a heat engine or gas engine, preferably a gas turbine.

In a preferred process, the electricity derived from the mechanical energy of the gas turbine and also that generated by the steam turbine are both used to power the separation and preferably the compression steps.

The paraffinic hydrocarbon feedstock may suitably be ethane, propane or butane. It may be substantially pure or may be in admixture with other hydrocarbons and optionally other materials, for example methane, nitrogen, carbon monoxide, carbon dioxide, steam or hydrogen. A paraffinic hydrocarbon-containing fraction such as naphtha, gas oil, vacuum gas oil, or mixtures thereof may be employed. A suitable feedstock is a mixture of gaseous paraffinic hydrocarbons, principally comprising ethane, resulting from the separation of methane from natural gas. Preferred is a paraffinic hydrocarbon principally comprising ethane which provides a product principally comprising ethylene as the mono-olefin.

As the molecular oxygen-containing gas there may suitably be used either oxygen or air. It is preferred to use oxygen, optionally diluted with an inert gas, for example nitrogen. It is preferred to pre-mix the oxygen-containing gas and the paraffinic hydrocarbon feedstock prior to contact with the catalyst. In the presence of a catalyst the composition of the gaseous paraffinic hydrocarbon/molecular oxygen-containing gas mixture is suitably from 5 to 13.5 times the stoichiometric ratio of hydrocarbon to oxygen-containing gas for complete combustion to carbon dioxide and water. The preferred composition is from 5 to 9 times the stoichiometric ratio of hydrocarbon to oxygen-containing gas.

Regarding the first step, the catalyst may be any catalyst capable of supporting combustion beyond the fuel rich limit of flammability. The catalyst may comprise a Group VIII metal as its catalytic component. Suitable Group VIII metals include platinum, palladium, ruthenium, rhodium, osmium and iridium. Rhodium, and more particularly, platinum and palladium are preferred. Typical Group VIII metal loadings range from 0.01 to 100 wt %, preferably, between 0.01 to 20 wt %, and more preferably, from 0.01 to 10 wt % based on the total dry weight of the catalyst.

Where a Group VII catalyst is employed, it is preferably employed in combination with a catalyst promoter. The promoter may be a Group IIIA, IVA, and/or VA metal. Alternatively, the promoter may be a transition metal; the transition metal promoter being a different metal to that which may be employed as the Group VIII transition metal catalytic component.

Preferred Group IIIA metals include Al, Ga, In and Tl. Of these, Ga and In are preferred. Preferred Group IVA metals include Ge, Sn and Pb. Of these, Ge and Sn are preferred. The preferred Group VA metal is Sb. The atomic ratio of Group VIII B metal to the Group IIIA, IVA or VA metal may be 1:0.1-50.0, preferably, 1:0.1-12.0.

Suitable metals in the transition metal series include those metals in Group IB to VIII of the Periodic Table. In particular, transition metals selected from Groups IB, IIB, VIB, VIIB and VIII of the Periodic Table are preferred. Examples of such metals include Cr, Mo, W, Fe, Ru, Os, Co, Rh, Ir, Ni, Pt, Cu, Ag, Au, Zn, Cd and Hg. Preferred transition metal promoters are Mo, Rh, Ru, Ir, Pt, Cu and Zn. The atomic ratio of Group VIII metal to transition metal promoter may be 1:0.1-50.0, preferably, 1:0.1-12.0.

Preferably, the catalyst comprises only one promoter; the promoter being selected from Group IIIA, Group IVA, Group VB and the transition metal series. For example, the catalyst may comprise a metal selected from rhodium, platinum and palladium and a promoter selected from the group consisting of Ga, In, Sn, Ge, Ag, Au or Cu. Preferred examples of such catalysts include Pt/Ga, Pt/In, Pt/Sn, Pt/Ge, Pt/Cu, Pd/Sn, Pd/Ge, Pd/Cu and Rh/Sn. The Rh, Pt or Pd may comprise between 0.01 and 5.0 wt %, preferably, between 0.01 and 2.0 wt %, and more preferably, between 0.05 and 1.0 wt % of the total weight of the catalyst. The atomic ratio of Rh, Pt or Pd to the Group IIIA, IVA or transition metal promoter may be 1:0.1-50.0, preferably, 1:0.1-12.0. For example, atomic ratios of R 1:0.1-12.0, more preferably, 1:0.2-3.0 and most preferably, 1:0.5-1.5. Atomic ratios of Pt or Pd to Ge, on the other hand, may be 1:0.1 to 50, preferably, 1:0.1-12.0, and more preferably, 1:0.5-8.0. Atomic ratios of Pt or Pd to Cu maybe 1:0.1-3.0, preferably, 1:0.2-2.0, and more preferably, 1:0.5-1.5.

Alternatively, the promoter may comprise at least two metals selected from Group IIIA, Group IVA and the transition metal series. For example, where the catalyst comprises platinum, the platinum may be promoted with two metals from the transition metal series, for example, palladium and copper. Such Pt/Pd/Cu catalysts may comprise palladium in an amount of 0.01 to 5 wt %, preferably, 0.01 to 2 wt %, and more preferably, 0.01 to 1 wt % based on the total weight of the dry catalyst. The atomic ratio of Pt to Pd maybe 1:0.1-10.0, preferably, 1:0.5-8.0, and more preferably, 1:1.0-5.0. The atomic ratio of platinum to copper is preferably 1:0.1-3.0, more preferably, 1:0.2-2.0, and most preferably, 1:0.5-1.5.

Where the catalyst comprises platinum, it may alternatively be promoted with one transition metal, and another metal selected from Group IIIA or Group IVA of the periodic table. In such catalysts, palladium may be present in an amount of 0.01 to 5 wt %, preferably, 0.01 to 2.0 wt %, and more preferably, 0.05-1.0 wt % based on the total weight of the catalyst. The atomic ratio of Pt to Pd may be 1:0.1-10.0, preferably, 1:0.5-8.0, and more preferably, 1:1.0-5.0. The atomic ratio of Pt to the Group IIIA or IVA metal may be 1:0.1-60, preferably, 1:0.1-50.0. Preferably, the Group IIIA or IVA metal is Sn or Ge, most preferably, Sn.

For the avoidance of doubt, the Group VIII metal and promoter in the catalyst may be present in any form, for example, as a metal, or in the form of a metal compound, such as an oxide.

It should be understood that actual concentrations of metal in the catalysts tend not to be identical to the nominal concentrations employed in the preparation of the catalyst because not all the metal employed during the preparation of the catalyst actually becomes incorporated in the catalyst composition. Thus, the nominal metal concentrations may have to be varied to ensure that the desired actual metal concentrations are achieved.

The autothermal cracking catalyst may be unsupported, such as in the form of a metal gauze, but is preferably supported. Any suitable support may be used such as ceramic or metal supports, but ceramic supports are generally preferred. Where ceramic supports are used, the composition of the ceramic support may be any oxide or combination of oxides that is stable at high temperatures of, for example, between 600° C. and 1200° C. The support material preferably has a low thermal expansion co-efficient, and is resistant to phase separation at high temperatures.

Suitable ceramic supports include corderite, lithium aluminium silicate (LAS), alumina ($\alpha$-$Al_2O_3$), yttria stabilised zirconia, alumina titanate, niascon, and calcium zirconyl phosphate. The ceramic supports may be wash-coated, for example, with $\gamma$-$Al_2O_3$ .

The autothermal cracking catalyst may be prepared by any method known in the art. For example, gel methods and wet-impregnation techniques may be employed. Typically, the support is impregnated with one or more solutions comprising the metals, dried and then calcined in air. The support may be impregnated in one or more steps. Preferably, multiple impregnation steps are employed. The support is preferably dried and calcined between each impregnation, and then subjected to a final calcination, preferably, in air. The calcined support may then be reduced, for example, by heat treatment in a hydrogen atmosphere. The reaction may be suitably carried out at a catalyst exit temperature of between 600° C. and 1200° C., preferably between 850° C. and 1050° C. and most preferably, between 900° C. and 1000° C.

The autothermal cracker may be operated at atmospheric or elevated pressure. Pressures of 1 to 40 barg may be suitable, preferably a pressure of 1-5 barg e.g. 1.8 barg is employed. However a total pressure of greater than 5 barg may be used, usually a total pressure of greater than 15 barg. Wherein the autothermal cracking is operated in a pressure range of between 15-40 barg, advantageously between 20-30 barg e.g. 25 barg the need for compression of the product. stream to facilitate separation and purification is reduced and preferably eliminated completely.

The autothermal cracker may suitably be operated at a temperature greater than 500° C., for example greater than 650° C., typically greater than 750° C., and preferably greater than 800° C. The upper temperature limit may suitably be up to 1200° C., for example up to 1100° C., preferably up to 1000° C. The catalyst exit temperature may suitably be in the range 600° C. to 1200° C., preferably in the range 850° C. to 1050° C. and, most preferably, in the range 900° C. to 1000° C.

It is preferred, although not essential, to preheat the feedstock and the oxygen-containing gas to suitably 200 to 500° C., preferably 200-300° C.

Preferably, the gaseous feedstock and the molecular oxygen-containing gas are fed to the autothermal cracker in admixture under a Gas Hourly Space Velocity (GHSV) of greater than 80,000 hr$^{-1}$ in order to minimise the formation of carbon monoxide and carbon dioxide. Preferably, the GHSV exceeds 200,000 hr$^{-1}$, especially greater than 1,000,000 hr$^{-1}$. For the purposes of the present invention GHSV is defined as—vol. of total feed at NTP/Time/(vol. of catalyst bed).

For further details of preferred methods of operation reference may be made to the aforesaid EP-B1-0332289; EP-B1-0529793; and EP-A-0709446.

Any coke produced in the autothermal cracking process may be removed by mechanical means, or by using one of the decoking methods such as that described in EP-A-0709446, the contents of which are hereby incorporated by reference.

The reaction products are quenched as they emerge from the reaction chamber to avoid further reactions taking place. The heat from the quenching is used to generate high-pressure steam, which is used to provide power for those parts of the overall process requiring it.

The cracked gases are then compressed, before being separated. In addition to mono-olefins and synthesis gas, the cracking reaction produces small amounts of acetylenes, aromatics and carbon dioxide. The carbon dioxide is usually removed, typically using an amine-based absorption system such as MEA or TEA (or mixtures of both), or any other commercially available $CO_2$ removal process. The cracked gases are then treated in a cryogenic separation unit, as is well known in the art.

One of the products of the separation unit is fuel gas (light gases including methane and hydrogen), and in a preferred embodiment this is fed to the gas turbine of a combined cycle cogeneration unit. In a typical cogeneration unit, the gas turbine consists of compressor and expander sections. Combustion air enters the compressor and is then contacted with the fuel in a combustion chamber. The hot combustion gases flow through the expander to provide the energy for the compressor and to drive an associated electric generator. Energy in the hot exhaust gases from the gas turbine is recovered by generation of high-pressure steam. This steam is used to produce additional electricity through a steam turbine. The overall efficiency of this system in converting fuel energy into electrical energy is about 50-55%, approximately double that of a typical steam cycle.

Advantageously the electrical power generated from the gas turbine and the steam turbine in the cogeneration unit is used to power the compressor employed in the cryogenic separation unit, the compressors used for compressing the cracked gas, and also the compressors used in the air separation plant which provides the oxygen for the autothermal cracking reaction.

BRIEF DESCRIPTION OF THE DRAWINGS

A preferred embodiment of the invention is described below with reference to the accompanying drawings, in which.

DETAILED DESCRIPTION OF PREFERRED EMBODIMENTS

Figure 1:
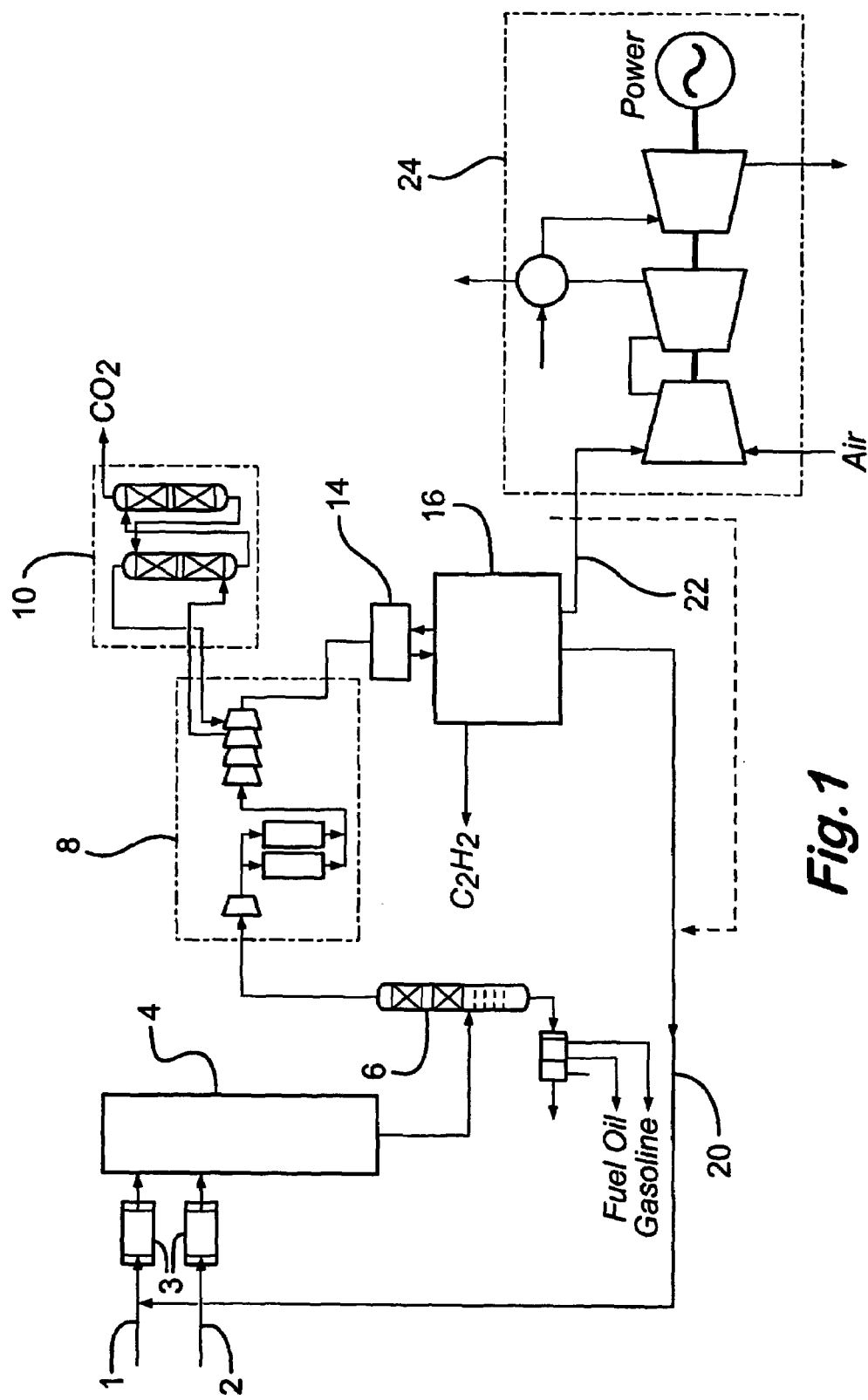
FIG. 1 is a simplified flow chart of the process of the embodiment.

Referring to FIG. 1, a paraffinic hydrocarbon feedstock principally comprising ethane and also oxygen are fed through lines 1 and 2 respectively via preheaters 3 to the autothermal cracker 4. Also fed to the autothermal cracker through line 2 is oxygen. The autothermal cracker 4 is maintained under conditions whereby oxidative dehydrogenation is effected to produce ethylene, higher olefins, methane, carbon dioxide, and syngas (carbon monoxide and hydrogen). The cracked gases are then quenched in order to prevent further reactions in a quench tower 6, and liquids comprising fuel oil and gasoline separated off. Following quenching, the cracked gases are compressed in a series of compressors 8 before being passed to an initial separation zone 10 where $CO_2$ is removed from the stream using an amine absorption system.

The compressed gases are passed through a refrigeration unit 14 before entering the separation and distillation unit 16, where they are separated into the various products. C2 products are split to obtain ethylene, with any ethane being recycled via line 20. Fuel gas from the separation unit is fed via line 22 to the gas turbine of a combined cycle cogeneration unit 24, which produces electrical power from the gas turbine and also a steam turbine in a known manner. This power, together with power generated by high pressure steam from the quenching in quench tower 6, drives the compressors 8 as well as the refrigerator compressor 14 and the oxygen separation unit for oxygen line 2.

Because in the autothermal cracking process there is no firebox or radiant/convective section as is found in a conventional olefins furnace, the amount of high-pressure steam generated in the cracking reaction and subsequent quenching is substantially less than in a conventional system. Consequently the proportion of the overall energy requirements supplied from other sources is greater than in a conventional system—approximately 68%, compared with less than 40% in a conventional steam cracking process. Accordingly the potential overall energy saving possible from using a cogeneration unit to provide this auxiliary supply is correspondingly greater.

Figure 2:
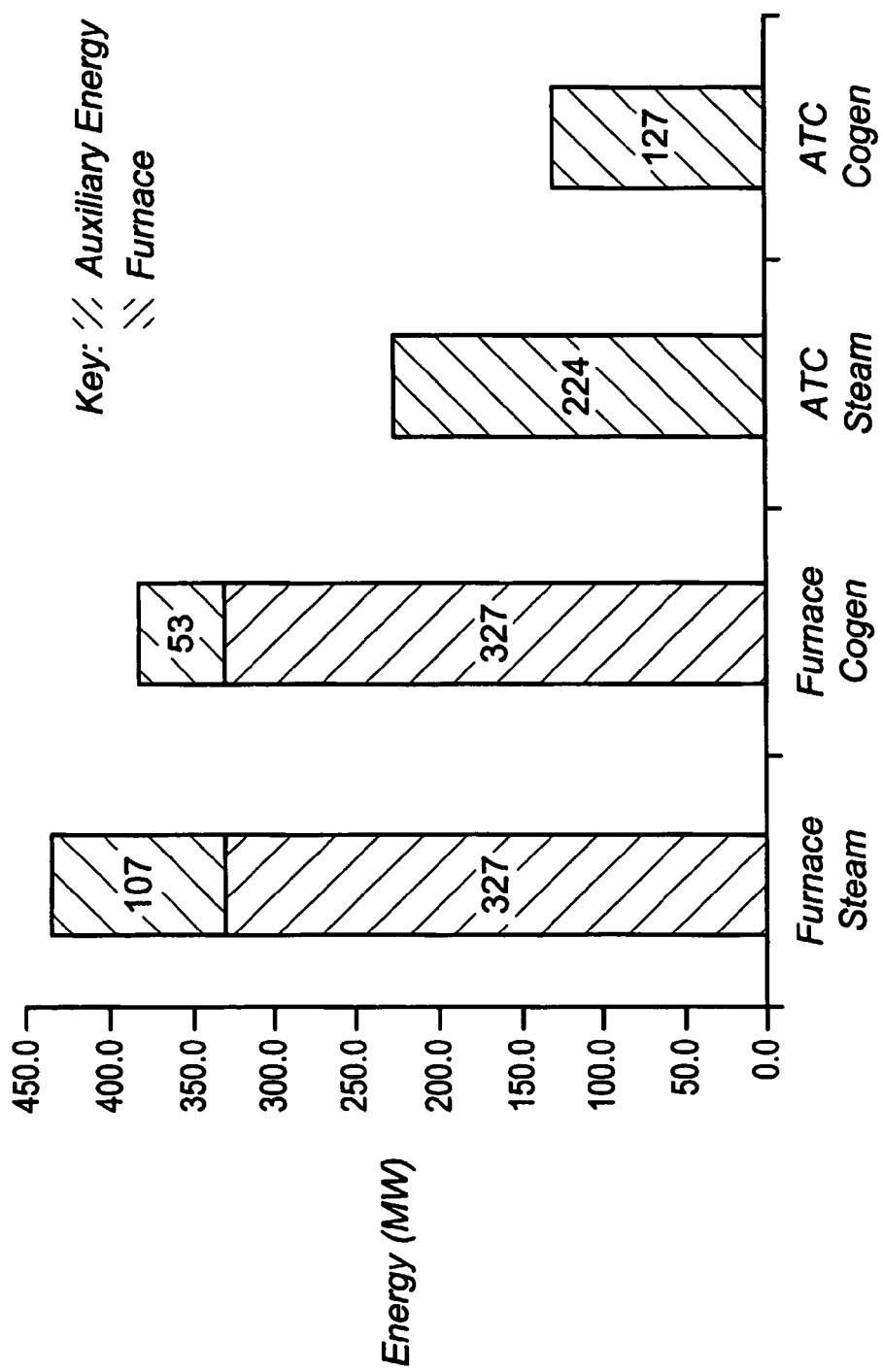
FIG. 2 shows theoretical fuel requirements for the process of the invention compared with other processes.

This is shown in FIG. 2, which shows the theoretical overall fuel requirements for conventional furnace-based and also autothermal cracking plants, for both conventional steam cycles as the auxiliary energy source, and alternatively cogeneration. A conventional furnace-based plant using steam cycles as the auxiliary energy source has a total theoretical energy requirement of 434 MW, which could be reduced to 380 MW by incorporating a cogeneration unit, a saving of a little over 10%. An autothermal cracking plants however, with a total energy requirement of 224 MW using steam cycles, can reduce this to 127 MW by using cogeneration according to the invention—a saving of around 40%. Accordingly it can be seen that using cogeneration benefits the autothermal cracking plant much more than it does a furnace-based plant. Overall fuel savings on the order of 50-75% can be achieved by combining autothermal cracking and cogeneration in an olefins plant.

A further benefit of the invention is that the reduction in fuel requirement also leads to a reduction in greenhouse gas (GHG) emissions. Compared with a typical olefins plant it is estimated that GHG emissions can be reduced by up to 40% with the combination of ATC and cogeneration. The reduction in greenhouse gases is not as great as the reduction in fuel use because some of the fuel used in the conventional plant is hydrogen (which does not produce GHG), and some of the fuel used in the autothermal cracking plant contains carbon monoxide, which produces incrementally more GHG.

The invention claimed is:

1. A process for the production of mono-olefins from a paraffin-containing hydrocarbon feed, comprising partially combusting a mixture of the hydrocarbon feed and a molecular oxygen-containing gas in contact with a catalyst capable of supporting combustion beyond the normal fuel rich limit of flammability and subsequently separating the products of said combustion wherein energy for the separation is provided by a cogeneration process which uses both a steam turbine and a gas turbine, and which simultaneously produces thermal energy and mechanical energy by combustion of fuel in the gas turbine, the mechanical energy being converted to electricity, and the thermal energy being used to create steam for use in the steam turbine to produce additional electricity.

2. A process according to claim 1 wherein prior to separating the products of said combustion the products are compressed and wherein the energy for the compression is also provided by the cogeneration process.

3. A process according to claim 1 wherein the fuel for the cogeneration comprises one of the products of the separation process.

4. A process according to claim 1 wherein the electricity derived from the mechanical energy of the gas turbine and also that generated by the steam turbine are both used to supply energy to the separation.

5. A process according to claim 2 wherein the electricity derived from the mechanical energy of the gas turbine and also that generated by the steam turbine are both used to supply energy to the separation and preferably the compression step.

6. A process according to claim 1 wherein the paraffin containing hydrocarbon feed is selected from the group consisting of ethane, propane, butane and mixtures thereof.

7. A process according to claim 6 wherein the paraffin containing hydrocarbon feed is ethane.

8. A process according to claim 1 wherein the mixture of the hydrocarbon feed and the molecular oxygen-containing gas is partially combusted at a pressure of between 1-40 barg.

9. A process according to claim 1 wherein the mixture of the hydrocarbon feed and the molecular oxygen-containing gas is partially combusted at a temperature of greater than 500° C.

10. A process according to claim 1 wherein the paraffin containing hydrocarbon feed and the oxygen-containing gas are preheated to between 200 to 500° C.

11. A process according to claim 1 wherein the separation unit produces fuel gas which is fed to the gas turbine of a combined cycle cogeneration unit.

* * * * *